United States Patent [19]
Satoshi et al.

[11] Patent Number: 5,369,021
[45] Date of Patent: Nov. 29, 1994

[54] MICROORGANISM FOR SELECTIVE PRODUCTION OF A SPECIFIC COMPOUND OF AVERMECTIN AND A METHOD FOR SELECTIVE PRODUCTION THEREOF

[75] Inventors: Ōmura Satoshi; Ikeda Haruo, both of Tokyo, Japan

[73] Assignee: The Kitasato Institute, Tokyo, Japan

[21] Appl. No.: 998,861

[22] Filed: Dec. 30, 1992

Related U.S. Application Data

[62] Division of Ser. No. 565,448, Aug. 10, 1990, Pat. No. 5,206,155.

[30] Foreign Application Priority Data

Mar. 5, 1990 [JP] Japan .................. 2-53411

[51] Int. Cl.$^5$ .................. C12P 1/04; C12P 7/22; C12P 17/02
[52] U.S. Cl. .................. 435/71.3; 435/41; 435/71.1; 435/71.2; 435/76; 435/117; 435/118; 435/123; 435/886; 435/240.1; 435/253.5; 435/119; 514/30; 514/161; 514/450
[58] Field of Search .................. 435/41, 76, 117, 118, 435/119, 123, 886, 240.1, 253.5, 71.1, 71.2, 71.3; 514/450, 30, 161

[56] References Cited

U.S. PATENT DOCUMENTS 4,310,519  1/1982  Albers-Schonberg .............. 424/181

FOREIGN PATENT DOCUMENTS 0276103  7/1988  European Pat. Off. .
0313297  4/1989  European Pat. Off. .

Primary Examiner—Michael G. Wityshyn
Assistant Examiner—Jane Williams
Attorney, Agent, or Firm—Jacobson, Price, Holman & Stern

[57] ABSTRACT

A microorganism for selective production of a specific compound of avermectin having one or more of the following properties:
- specific accumulation of avermectin compound "a",
- effective incorporation of isoleucine or its keto acid (3-methyl-2-oxovaleric acid) into avermectin molecule, and
- markedly suppressed incorporation of valine or its keto acid (2-oxoisovaleric acid) into avermectin molecule.

9 Claims, 4 Drawing Sheets

RETENTION TIME (min)

MICROORGANISM FOR SELECTIVE PRODUCTION OF A SPECIFIC COMPOUND OF AVERMECTIN AND A METHOD FOR SELECTIVE PRODUCTION THEREOF

This is a divisional of application Ser. No. 07/565,448 filed Aug. 10, 1990, now U.S. Pat. No. 5,206,155.

FIELD OF THE INVENTION

This invention relates to a microorganism belonging to genus Streptomyces for selective production of a specific compound of avermectin having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure. More particularly the present invention concerns a process for selective production of a specific compound of avermectin using a microorganism belonging to genus Streptomyces which is defective in avermectin B O-methyltransferase activity.

THE PRIOR ARTS

Avermectins are an antibiotic having anthelmintic activity produced by *Streptomyces avermitilis*. In cultured medium of the said microorganism, eight compounds of avermectin, $A_{1a}$, $A_{2a}$, $B_{1a}$, $B_{2a}$, $A_{1b}$, $A_{2b}$, $B_{1b}$ and $B_{2b}$, are produced (U.S. Pat. No. 4,310,519). Compounds "A" and "B" have substituent methoxy or hydroxy at C-5, respectively. A compound group "1" has double bond at C-22 and C-23, and group "2" has hydrogen at C-22 and hydroxy at C-23. An "a" group compound has substituent sec-butyl at C-25, and a "b" group compound has substituent isopropyl at C-25. Among these 22, 23-dihydroavermectin $B_1$ (Ivermectin), a hydrogenated product of $B_1$ compound, is used as an anthelmintic.

In the prior art, avermectin has been produced by culturing *Streptomyces avermitilis* in a medium consisting of an assimilable nitrogen source, carbon source and inorganic salt under aerobic conditions to produce analogous structure eight compounds of avermectin $A_{1a}$, $A_{2a}$, $B_{1a}$, $B_{2a}$, $A_{1b}$, $A_{2b}$, $B_{1b}$ and $B_{2b}$. Extracting the product with an organic solvent, a mixture of avermectins, are separated to a fraction of $A_1$, $A_2$, $B_1$ and $B_2$, then purified to obtain $B_1$ fraction, which is a mixture of $B_{1a}$ and $B_{1b}$, thereafter the $B_1$ fraction is hydrogenated to manufacture 22, 23-dihydroavermectin $B_1$.

The prior art has number of disadvantages. Namely, the eight compounds have to be produced as a mixture. Furthermore an industrial scale separation of "a" and "b" compounds are quite difficult, thereby an efficient production of $B_{1a}$ component with good yield and low cost has strongly been requested.

SUMMARY OF THE INVENTION

We have found that avermectin $B_{1a}$ and $B_{2a}$ compounds can effectively be obtained by using a microorganism strain having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure, to which adding a deficiency of avermectin B O-methyltransferase activity. Separation of avermectin $B_{1a}$ (a double bond between C-22 and C-23) and $B_{2a}$ (OH at C-23) compounds can easily be made by chromatography.

OBJECTS OF THE INVENTION

An object of the present invention is to provide a process for selective production of a specific compound of avermectin which comprises culturing a microorganism belonging to Streptomyces and having the properties of specific accumulation of avermectin compound "a", effective incorporation of isoleucine or its keto acid (3-methyl-2-oxovaleric acid) into avermectin structure, and markedly suppressed incorporation of valine or its keto acid (2-oxoisovaleric acid), to which adding a deficiency of avermectin B O-methyltransferase activity, in a medium, accumulating avermectin $B_{1a}$ and $B_{2a}$ in a medium, and isolating avermectin $B_{1a}$ and $B_{2a}$ from the cultured mass.

Another object of the present invention is to provide a microorganism belonging to *Streptomyces avermitilis* for selective production of specific compound of avermectin having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure, to which adding a deficiency of avermectin B O-methyltransferase activity.

DETAILED DESCRIPTION OF THE INVENTION

Figure 1A:
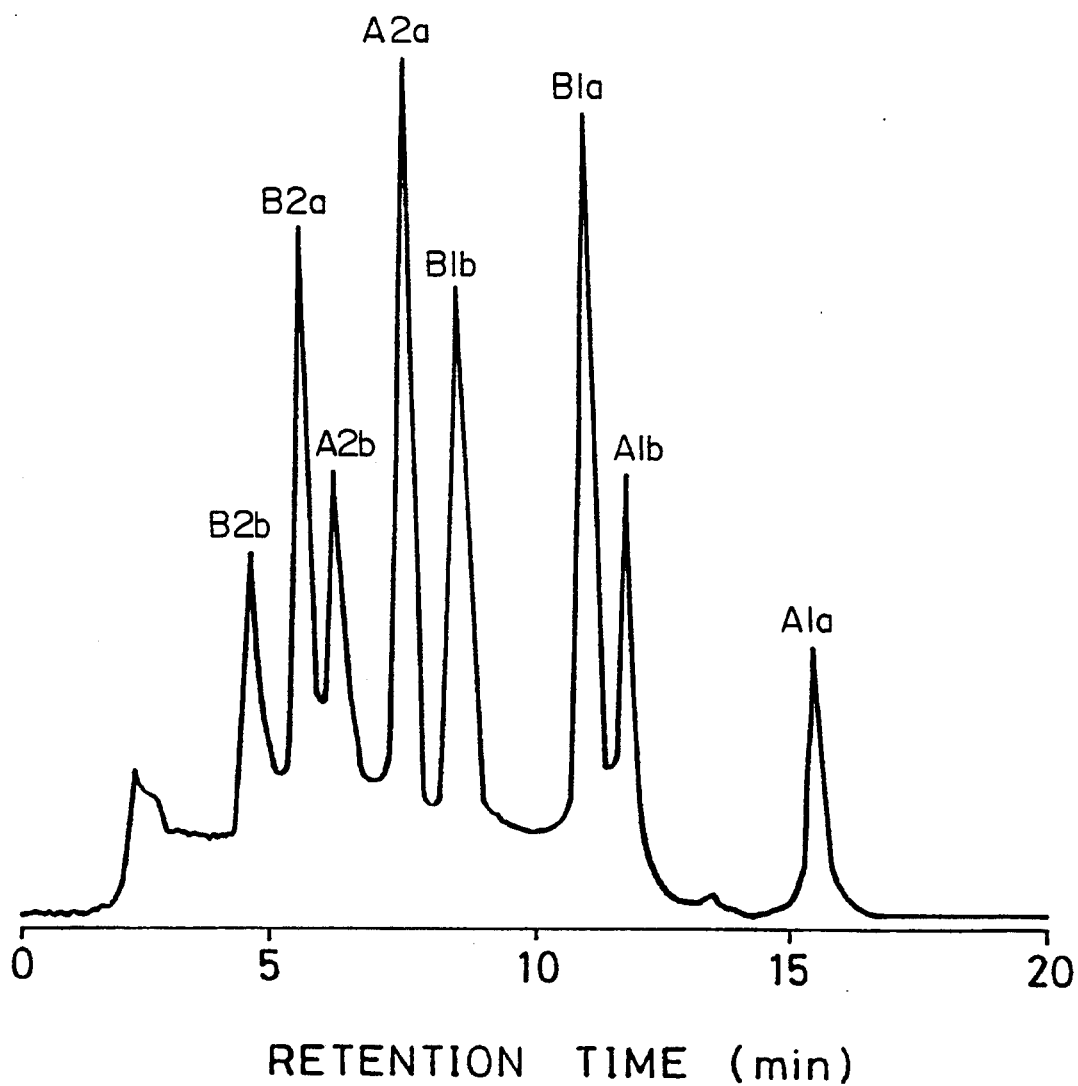
FIG. 1A shows the HPLC pattern of a cultured material of *Streptomyces avermitilis* ATCC 31271.

No report has been known on the effective accumulation of specific compound of avermectin by a fermentation method without feeding additives in a medium during culture using microorganism belonging to *Streptomyces avermitilis* to which the deficient nature is incorporated.

The microorganisms having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure, to which adding a deficiency of avermectin B O-methyltransferase activity, can be used in the present invention whether it is obtained from natural sources or mutant having auxotrophic nature or drug resistance, and can be included in the present invention. The present invention also includes microorganisms, a mutant having the properties described in the present specification, which are improved by recombinant DNA techniques, transformation or transduction.

The preferable example of microorganism used in the present invention is *Streptomyces avermitilis* K 2038 which is derived from *Streptomyces avermitilis* ATCC 31271, and is a mutant wherein protoplasts of a mutant K 2033 having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure, and a mutant K 2034 having a deficient nature of avermectin B O-methyl-transferase activity, are fused. Namely strain K 2038 is a mutant in which a deficient nature of avermectin B O-methyl-transferase activity is introduced into a strain K 2033. These mutant strains, *Streptomyces avermitilis* K 2033, K 2034 and K 2038, have been deposited in the Fermentation Research Institute, Agency of Industrial Science and Technology, M.I.T.I. 1–3, Higashi, 1 chome Tsukuba-shi, Ibaraki-ken 305, Japan, according to Budapest Treaty as FERM BP-2773, FERM BP-2774 and FERM BP-2775, respectively by the assignee, Kitasato Institute on Feb. 26, 1990.

Induction in mutation can easily be performed by conventional mutation techniques. Preferably, original strain is treated by ultraviolet irradiation or with a mutagen such as N-methyl-N'-nitro-N-nitrosoguanidine or ethyl methanesulfonic acid, thereafter treated colonies are cultured in a medium, in which labeled isoleucine or its keto acid (3-methyl-2-oxo-valeric acid) and labeled valine or its keto acid (2-oxo-isovaleric acid) are added and the culture is further continued for several hours. Avermectin fraction is isolated from cultured mycelia and radioactivity of avermectin is measured, thereby mutants having properties of an effective incorporation of isoleucine or its keto acid (3-methyl-2-oxovaleric acid) into avermectin structure, and significantly suppressed incorporation of valine or its keto acid (2-oxoisovaleric acid) into avermectin structure, are selected.

A mutant deficient in avermectin B O-transferase activity can be obtained by treatment of mutagen as same as of the above, and the thus obtained colonies are cultured in avermectin production medium. Cultured mycelia are extracted with organic solvent and the extract is separated by silica-gel thin layer chromatography. Then the mutant which can merely produce avermectin B can be selected.

An introduction of the deficiency of avermectin B O-methyltransferase activity by a protoplast fusion technique can be performed by that a protoplast prepared from a mutant having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxo-isovaleric acid) into avermectin structure, and a protoplast prepared from a mutant having the properties of deficient in avermectin B O-methyltransferase activity, are fused with using polyethylene glycol, then the fused protoplast is regenerated to mycelia in a suitable regeneration medium. Thus regenerated colonies having the properties of accumulating avermectin compound "a" and deficient in avermectin B O-methyl-transferase activity are selected.

In a production of avermectin $B_{1a}$ and $B_{2a}$, the mutant strain having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure, and having a deficient nature of avermectin B O-methyltransferase activity, are cultured in a medium. A medium for production of avermectin $B_{1a}$ and $B_{2a}$ is a conventional medium which contains carbon source, nitrogen source and inorganic salts. Examples of carbon source are glucose, glycerin, sucrose, dextrin, starch or molasses. Examples of nitrogen source are casein, casein hydrolyzate, yeast extract, autolyzed yeast, yeast hydrolyzate, dry yeast, soy bean powder, soy bean digestible, corn steep liquor, distiller's soluble, cotton seed powder or meat extract. Examples of inorganic salts are phosphate, sulfate, nitrate, chloride or carbonate of sodium, potassium, magnesium, ammonium, calcium, manganese, zinc, iron or cobalt, and a conventional salt which can generate these ions. Cultivation can be proceeded under aerobic condition. Fermentation can be proceeded by controlling the medium at pH 5–9, at 25°–35° C., for 120–192 hours shaking culture under aerobic condition. If the production of avermectin $B_{1a}$ is desired, an avermectin producing strain which can accumulate avermectin $B_{1a}$ should naturally be selected.

Avermectin $B_{1a}$ and $B_{2a}$ can be isolated from cultured mass by a conventional isolation method for antibiotics. For example, a composition containing avermectins is extracted the filtered mycelia with organic solvent such as acetone or methanol, which is concentrated after filtration. The concentrate is further extracted with organic solvent such as methylenechloride. Organic layer was concentrated in vacuo to obtain avermectin $B_{1a}$ and $B_{2a}$. Avermectin $B_{1a}$ can be separated by treating the concentrate with column chromatography using ion-exchanger, silica-gel, reverse phase silica-gel or Sephadex, or counter current distribution method. For example, a mixture containing avermectin $B_{1a}$ is treated by preparative HPLC (reverse phase silica-gel, ODS) with migration phase of 80% v/v methanol/water to elute avermectin $B_{1a}$. The extract is concentrated in vacuo and recrystallized from methanol to obtain avermectin $B_{1a}$ in a pure form.

Following examples illustrate the present invention but are not construed as limiting.

Isolation of a mutant having the properties of specific accumulation of avermectin compound "a", an effective incorporation of isoleucine or its keto acid (3-methyl-2-oxovaleric acid) into avermectin structure, and markedly suppressed incorporation of valine or its keto acid (2-oxoisovaleric acid) into avermectin structure:

EXAMPLE 1

Spores of *Streptomyces avermitilis* ATCC 31271 treated with conventional method by N-methyl-N'-nitro-N-nitrosoguanidine (1 mg/ml, pH 9.0 at 30° C. for 60 min.) treatment were diluted with sterilized water for approximately 200 colonies per plate, spread on YMS plate and cultured at 30° C. for 5 days. The colonies were picked up and inoculated patchily onto YMS plate with 1 cm$^2$ square, for which was set up as a master plate. Each colony on the master plate was inoculated into a 100 ml Erlenmeyer flask containing 10 ml of culture medium, and cultured at 28° C. with 210 rpm, amplitude 2.5 cm for 96 hours. [U—$^{14}$C]-L-isoleucine (50,000 cpm) and [3,4-$^3$H]-L-valine (100,000 cpm) were added thereto and further cultured for 6 hours. Cultured mycelia were collected and extracted with 3 ml acetone. The acetone extract was dried in vacuo. Crude extract dissolved in a small amount of methanol was spotted on a silica-gel thin layer plate (Merck Kiesel gel 60F$_{254}$) and developed with 15% v/v isopropanol/hexane. After checking avermectin spot by UV irradiation at 254 nm, the part thereof was cut and put into 15 ml scintillation vial, added 0.5 ml methanol, and shaked at room temperature for 10 minutes to extract avermectin from silica-gel. 5 ml scintillator (10 g 2,5-diphenyloxazol, 0.2 g p-bis(O-methylstyryl) benzene and 1 l xylene) was added therein and radioactivity of each sample was measured by liquid scintillation spectrometer. *Streptomyces avermitilis* ATCC 31271 was used as a control.

EXAMPLE 2

A corresponding mutant having the properties of an effective incorporation of [U—$^{14}$C]-L-isoleucine into avermectin structure, and markedly suppressed incorporation of [3,4-$^{3}$H]-L-valine into avermectin structure, was collected from the master plate and cultured as same as of in Example 1. An equal amount as of in Example 1 of [U—$^{14}$C]-L-isoleucine and [3,4-$^{3}$H]-L-valine, or [U—$^{14}$C]-3-methyl-2-oxovaleric acid and [3,4-$^{3}$H]-2-oxoisovaleric acid were added and cultured for 6 hours. Avermectin fraction was isolated as same as of in Example 1 and the radio activity was measured. Result is shown in Table 1. Labeled compound was incorporated into avermectin structure by an original strain *Streptomyces avermitilis* ATCC 31271. On the other hand, a mutant strain K 2033 incorporated [U—$^{14}$C]-L-isoleucine or its keto acid (3-methyl-2-oxovaleric acid) effectively into avermectin structure, but incorporation of [3,4-$^{3}$H]-L-valine or its keto acid (2-oxoisovaleric acid) into avermectin structure was markedly decreased.

EXAMPLE 3

Figure 1B:
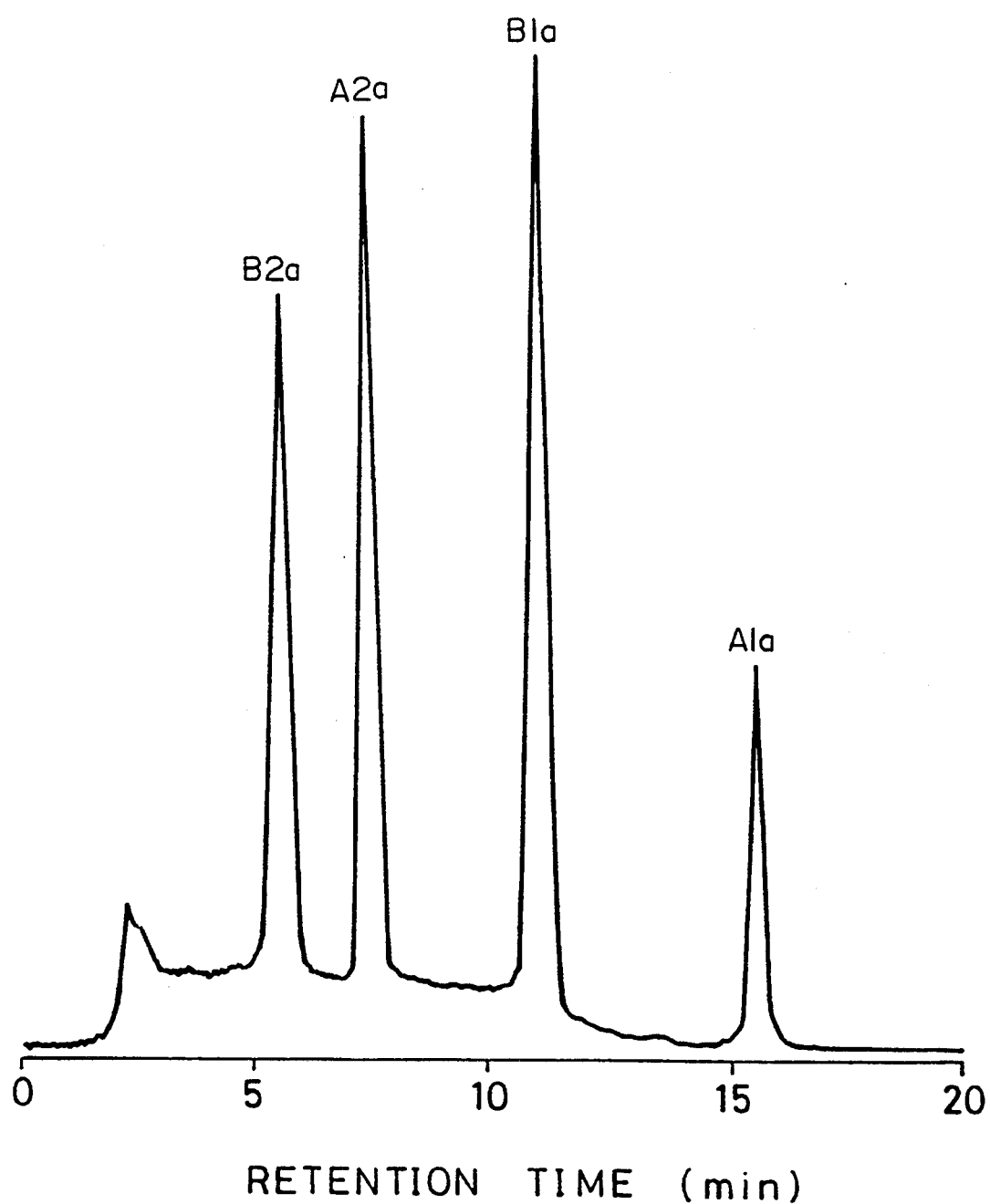
FIG. 1B shows the HPLC pattern of a cultured material of *Streptomyces avermitilis* K 2033.

Spore suspensions of the original strain *Streptomyces avermitilis* ATCC 31271 and strain K 2033 obtained in Example 2 were inoculated into 100 ml Erlenmeyer flask containing 10 ml production medium, and cultured at 28° C., 210 rpm, amplitude 2.5 cm, for 168 hours. Cultured mycelia was mixed with 10 ml methanol and extracted the avermectin. After removing mycelial residue by centrifugation, avermectin in the extract was analysed by HPLC (ODS 3 μm, column size 6φ×75 mm, speed 1 ml/min., mobility phase 80% v/v methanol/water, detection 246 nm). Result is shown in FIGS. 1A and 1B. An original strain *Streptomyces avermitilis* ATCC 31271 produced 8 compounds of avermectin ($A_{1a}$, $A_{1b}$, $A_{2a}$, $A_{2b}$, $B_{1a}$, $B_{1b}$, $B_{2a}$ and $B_{2b}$) and the mutant strain K 2033 produced 4 compounds of avermectin containing main effective compound $B_{1a}$ ($A_{1a}$, $A_{2a}$, $B_{1a}$ and $B_{2a}$).

Mutant strain defect in avermectin B O-methyltransferase

EXAMPLE 4

Spores of *Streptomyces avermitilis* ATCC 31271 treated with conventional method by N-methyl-N'-nitro-N-nitrosoguanidine (1 mg/ml, pH 9.0 at 30° C. for 60 min.) treatment were diluted with sterilized water for approximately 200 colonies per plate, spread on YMS plate and cultured at 30° C. for 5 days. The colonies were picked up and inoculated patchily onto YMS plate with 1 cm$^2$ square, for which was set up as a master plate. The master plate was replicated on the production medium 3 and incubated at 30° C. for 8 days. Each patchlike shape colony on the production medium 3 was cut-out together with agar medium, inserted into plastic tube, added 0.5 ml acetone therein and allowed to stand at room temperature for 15 minutes to extract the cultured product. After removing mycelia and agar strips, the acetone extract was dried in vacuo. Extract was dissolved in 25 μl acetone, and 5 μl thereof were spotted on a silica-gel thin layer plate (Merck, Kiesel gel 60F$_{254}$) then developed with 15% v/v isopropanol/hexane. A mutant strain K 2034 which produced only avermectin B compound was collected by means of UV irradiation at 254 nm.

Introduction of avermectin B O-methyltransferase deficient property into a strain K 2033 by protoplast fusion

EXAMPLE 5

A spore suspension of strain K 2033 obtained in Example 2 and avermectin B O-methyltransferase activity deficient strain K 2034 obtained by mutation of original strain ATCC 31271 was inoculated into 500 ml Erlenmeyer flask containing YEME medium (50 ml) including 30% w/v sucrose, 5 mM MgCl$_2$ and 0.5% w/v glycine, and cultured at 28° C., 180 rpm for 68 hours. Mycelia obtained by centrifugation of cultured liquid at 3000 rpm for 10 min. was suspended in P10 medium (10 ml) and re-centrifuged to collect mycelia. Washed mycelia were suspended in P10 medium (10 ml) containing egg white lysozyme (1 mg/ml) sterilized by filtration and gently shaked at 37° C. for 60 minutes to form protoplast. A sample containing the protoplast was filtered through cotton filter to remove undigested mycelia. Protoplast was sedimented by centrifugation at 3000 rpm for 10 minutes. Protoplast was gently suspended by adding P 20 medium (5 ml) thereafter again protoplast was collected by centrifugation. After resuspended the protoplastin P 20 medium (2 ml), a part of the suspension was diluted and dropped onto hemocytometer then number of protoplast was calcurated by phase-contrast microscope (×400). The protoplasts of a strain K 2033 and K 2034, each 5×10$^8$, respectively, were transferred into small test tube and mixed completely. Whole volume thereof was controlled below 50 μl. A solution (0.5 ml) of 50% w/v polyethylene glycol #1000 (1 g of polyethylene glycol #1000 dissolved in 1 ml of P 20 medium was filter-sterilized through 0.45 μm filter) was added therein and rapidly mixed to fuse the protoplasts. After allowed to stand at room temperature for 1 minutes, P 20 medium (0.5 ml) was added and mixed to dilute polyethylene glycol. A fusant was diluted with P 20 medium at 10$^{-2}$ and 10$^{-3}$, and 0.1 ml/plate of the fusant and 2.5 ml of soft agar RM14 were spread on RM14 medium. The plate was incubated at 30° C. for 10 days to regenerate mycelia. Mycelia was separated from the plate surface and homogenated by homogenizer. The mycelia was diluted with sterile water, spread on YMS plate and incubated at 30° C. for 5 days. Matured spore was scratched up, diluted with sterile water up to 200 colonies per plate, spread on YMS plate then incubated at 30° C. for 5 days. 80% of the budding colonies showed type of K 2033 strain (dark brown, abundant spores) and the other showed type of K 2034 strain (pale brown, few spores).

EXAMPLE 6

Colonies appearing analogous type of K 2033 strain obtained by protoplast fusion were spread patchily and incubated at 30° C. for 8 days. Patches of each colony were cut-out, inserted into plastic tubes, added acetone (0.5 ml) thereto and allowed to stand at room temperature for 15 minutes for extracting the product. Mycelia and agar strips were removed off and the extract was concentrated in vacuo. The thus obtained crude extract was dissolved in acetone (25 μl) and the solution (5 μl) was spotted on a silica-gel thin layer plate, then developed with 85% v/v hexane/isopropanol. Avermectin thus produced was checked by UV at 254 nm, then strains which produced avermectin B compound having deficient nature of avermectin B O-methyl transferase activity were selected. Further these extracts were spotted on a reversed phase silica-gel thin layer plate (Whatman KC18F), developed with 70% v/v acetonitrile/water, then strains merely producing avermectin "a" compound were selected by checking with UV at 254 nm.

EXAMPLE 7

Figure 2:
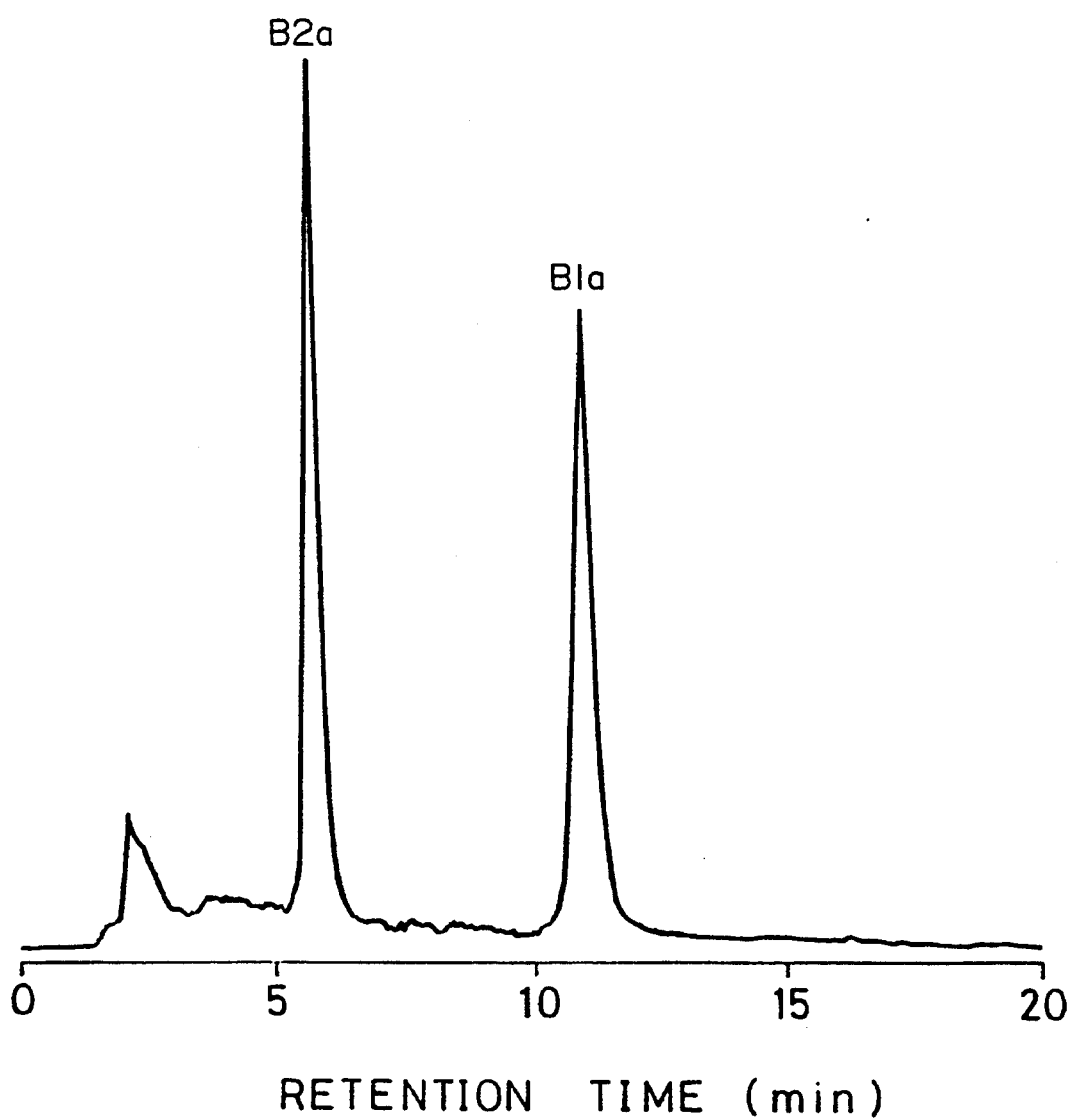
FIG. 2 shows the HPLC pattern of cultured material of *Streptomyces avermitilis* K 2038.

Spore suspension of a variant (K 2038 strain) which was obtained by protoplast fusion and was merely producing avermectin "a" compound in B compound, was inoculated in 50 ml large test tube containing 10 ml seed medium and shake cultured at 30° C. for 48 hours. A 0.2 ml thereof was inoculated into 100 ml Erlenmeyer flask containing 10 ml production medium 2 and cultured at 28° C. at 210 rpm, 2.5 cm amplitute for 168 hours. Cultured product was extracted by the same way as of in Example 3, then the extract was analysed. Result is shown in FIG. 2. A strain K 2038 obtained by protoplast fusion produced the active principles compounds $B_{1a}$ and $B_{2a}$ in the 8 compounds of avermectins. Furthermore amount of accumulation of avermectin $B_{1a}$ was significantly increased up.

EXAMPLE 8

Figure 3:
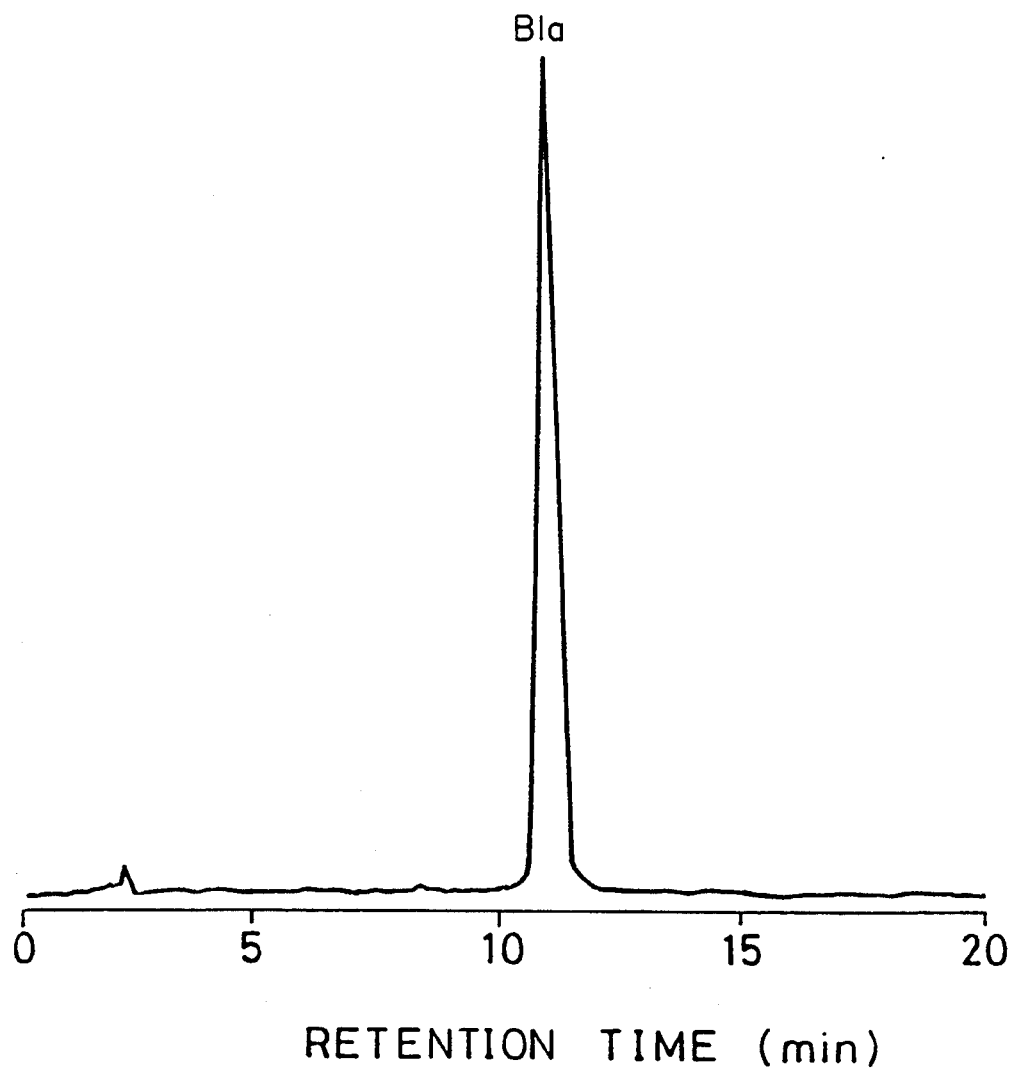
FIG. 3 shows the HPLC pattern purified product of cultured *Streptomyces avermitilis* K 2038.

Mycelia was separated from cultured mass (approx. 250 ml) of *Streptomyces avermitilis* K 2038 cultured in 30 Erlenmeyer flasks. After washing the mycelia with deionized water (150 ml), methanol (100 ml) was added thereto and stirred at room temperature for 30 minutes for extraction. Mycelial extract was filtered through Celite to remove mycelial residue, and the filtrate was concentrated up to approximately 10 ml in vacuo. Deionized water (10 ml) further methylenechloride (20 ml) were added to the concentrate for extraction. Methylene chloride layer was separated, thereafter further the water layer was extracted with methylene chloride (20 ml). Combined methylene chloride extract was dried up in vacuo and the residue was dissolved in ethyl acetate (50 ml) which was dehydrated by adding anhydrous sodium sulfate (2 g). Ethyl acetate solution was passed through silica-gel (10 g) column then eluted with ethyl acetate (50 ml). Eluate was collected and concentrated in vacuo to obtain viscous oily product (0.8 g). The oily substance (0.8 g) dissolved in small amount of methylene chloride was passed through a column of silica-gel (Merck 100–200 mesh) equilibrated with methylene chloride. After washing with methylene chloride, elution was carried out with 5% v/v isopropanol/methylene chloride. Fractions containing avermectin $B_{1a}$ was collected then passed through a column of active carbon (2 g). The column was further washed with methylene chloride (10 ml). The thus obtained eluate was dried up in vacuo, added thereto small amount of isopropyl ether to dissolve the material, thereafter hexane was added dropwise under cooling to obtain white precipitate. The precipitate was collected by filtration, dried in vacuo to obtain white powder (10 mg). According to analysis by HPLC the said white powder contained over 90% of avermectin $B_{1a}$. (refer to FIG. 3)

Physico-chemical properties of the thus obtained white powder is identical with those of avermectin $B_{1a}$ reported in J. Am. Chem. Soc., 103: 4216–4221 (1981).

Compositions of the media used in the foregoing examples are illustrated hereinbelow.

| YMS medium | |
|---|---|
| malt extract (Difco) | 10 g |
| yeast extract (Difco) | 4 g |
| soluble starch (Difco) | 4 g |
| agar | 20 g |
| distilled water | 1 l |

Adjusted to pH 7.2 with adding 2N KOH and sterilized at 121° C. for 15 minutes. After sterilization, magnesium chloride and calcium nitrate were added up to 10 mM and 8 mM, respectively.

| Production medium 1 | |
|---|---|
| glucose | 30 g |
| NaCl | 2.0 g |
| $KH_2PO_4$ | 0.05 g |
| $FeSO_4.7H_2O$ | 0.05 g |
| $ZnSO_4.7H_2O$ | 0.05 g |
| $MnSO_4.4H_2O$ | 0.05 g |
| $MgSO_4.7H_2O$ | 0.1 g |
| $(NH_4)_2SO_4$ | 1.5 g |
| $CaCO_3$ | 5.0 g |
| distilled water | 1 l |

Adjusted to pH 7.2 with 2N KOH, then sterilized at 121° C. for 15 min.

| Production medium 2 | |
|---|---|
| glucose | 45 g |
| peptonized milk (Oxoid) | 24 g |
| autolyzed yeast (Difco) | 2.5 g |
| polypropylene glycol #2000 | 2.5 ml |
| distilled water | 1 l |

Adjusted to pH 7.2 with 2N KOH, then sterilized at 121° C. for 15 minutes.

| Production medium 3 | |
|---|---|
| glucose | 45 g |
| peptonized milk (Oxoid) | 24 g |
| autolyzed yeast (Difco) | 2.5 g |
| agar | 20 g |
| distilled water | 1 l |

Adjusted to pH 7.2 with 2N KOH, then sterilized at 121° C. for 15 minutes.

| YEME medium | |
|---|---|
| yeast extract (Difco) | 3 g |
| malt extract (Difco) | 3 g |
| peptone (Difco) | 5 g |
| glucose | 10 g |
| distilled water | 1 l |

Sterilized at 121° C. for 15 minutes.

| Trace element solution | |
|---|---|
| $FeCl_3.6H_2O$ | 200 mg |
| $ZnCl_2$ | 40 mga |
| $CuCl_2.2H_2O$ | 10 mg |

| Trace element solution | |
|---|---|
| $MnCl_2 \cdot 4H_2O$ | 10 mg |
| $Na_2B_4O_7 \cdot 10H_2O$ | 10 mg |
| $(NH_4)_6Mo_7O_{24} \cdot 4H_2O$ | 10 mg |
| distilled water | 1 l |
| P 10 medium | |
| sucrose | 103 g |
| $K_2SO_4$ | 0.25 g |
| $MgCl_2 \cdot 6H_2O$ | 2.03 g |
| trace element solution | 2.0 ml |
| distilled water | 800 ml |

After sterilization at 121° C. for 15 minutes following mixture is added.

| 0.5% $KH_2PO_4$ | 10 ml |
|---|---|
| 3.68% $CaCl_2 \cdot 2H_2O$ | 100 ml |
| 0.25 M MES buffer solution pH 6.5 | 100 ml |
| P 20 medium | |
| sucrose | 205 g |
| $K_2SO_4$ | 0.25 g |
| $MgCl_2 \cdot 6H_2O$ | 2.03 g |
| trace element solution | 2.0 ml |
| distilled water | 800 ml |

After sterilization at 121° C. for 15 minutes following mixture is added.

| 0.5% $KH_2PO_4$ | 10 ml |
|---|---|
| 3.68% $CaCl_2 \cdot 2H_2O$ | 100 ml |
| 0.25 M MES buffer solution pH 6.5 | 100 ml |
| RM 14 medium | |
| sucrose | 205 g |
| $K_2SO_4$ | 0.25 g |
| $MgCl_2 \cdot 6H_2O$ | 10.12 g |
| glucose | 10.0 g |
| casamino acid | 0.1 g |
| L-proline | 3.0 g |
| yeast extract (Difco) | 2.0 g |
| trace element solution | 2.0 ml |
| oat meal agar (Difco) | 3.0 g |
| agar | 20 g |
| distilled water | 870 ml |

After sterilization at 121° C. for 15 minutes following mixture is added.

| 0.05% $KH_2SO_4$ | 10 ml |
|---|---|
| 3.68% $CaCl_2 \cdot H_2SO_4$ | 80 ml |
| 0.25 M MES buffer solution pH 6.5 | 40 ml |
| Soft agar RM 14 medium | |
| sucrose | 205 g |
| $K_2SO_4$ | 0.25 g |
| $MgCl_2 \cdot 6H_2O$ | 10.12 g |
| glucose | 10.0 g |
| casamino acid (Difco) | 0.1 g |
| L-proline | 3.0 g |
| yeast extract (Difco) | 2.0 g |
| trace element solution | 2.0 ml |
| oat meal agar (Difco) | 3.0 g |
| agar | 5.0 g |
| distilled water | 870 ml |

After sterilized at 121° C. for 15 minutes following mixture is added.

| 0.5% $KH_2PO_4$ | 10 ml |
|---|---|
| 3.68% $CaCl_2 \cdot 6H_2O$ | 80 ml |
| 0.25 M MES buffer solution pH 6.5 | 40 ml |

TABLE 1

| | Incorporation of labeled compound into avermectin (cpm) Additive | | | |
|---|---|---|---|---|
| strain | $(U-^{14}C)$-L-isoleucine | $(3, 4-^{3}H)$-L-valine | $(U-^{14}C)$-3-methyl-2-oxovaleric acid | $(3, 4-^{3}H)$-2-oxovaleric acid |
| ATCC31271 | 398 | 423 | 655 | 575 |
| K2033 | 512 | 22 | 927 | 25 |

What is claimed is:

1. A process for selective production of an avermectin compound "a", comprising the step of culturing a strain of *Streptomyces avermitilis* microorganism selected from the group consisting of *Streptomyces avermitilis* K 2038 (FERM BP-2775), *Streptomyces avermitilis* K 2033 (FERM BP-2773) and *Streptomyces avermitilis* K 2034 (FERM BP-2774) capable of producing essentially only avermectin compound "a" and wherein the culture retains the ability to degrade isoleucine or its keto acid (3-methyl-2-oxovaleric acid) but has a decreased ability to degrade valine or its keto acid (2-oxoisovaleric acid) in the avermectin pathway on an aqueous nutrient medium comprising an assimilable source of nitrogen, carbon and inorganic salt; and recovering the avermectin compound "a" from the medium.

2. The process of claim 1, further comprising the additional step of isolating avermectin $B_{1a}$ produced by said *Streptomyces avermitilis*.

3. The process of claim 1, further comprising the additional step of isolating avermectin $B_{1a}$ and $B_{2a}$ produced by said *Streptomyces avermitilis*.

4. The process of claim 1, wherein the strain has all identifying characteristics of *Streptomyces avermitilis* K 2033 (FERM BP-2773).

5. The process of claim 4, wherein the microorganism is *Streptomyces avermitilis* K 2033 (FERM BP-2773).

6. The process of claim 1, wherein the microorganism has all identifying characteristics of *Streptomyces avermitilis* K 2034 (FERM BP-2774).

7. The process of claim 6, wherein the microorganism is *Streptomyces avermitilis* K 2034 (FERM BP-2774).

8. The process of claim 1, wherein the microorganism has all identifying characteristics of *Streptomyces avermitilis* K 2038 (FERM BP-2775).

9. The process of claim 8, wherein the microorganism is *Streptomyces avermitilis* K 2038 (FERM BP-2775).

* * * * *